(12) United States Patent
Gillon et al.

(10) Patent No.: US 8,399,415 B2
(45) Date of Patent: *Mar. 19, 2013

(54) OLIGOPEPTIDES AND COSMETIC COMPOSITIONS CONTAINING THE OLIGOPEPTIDES

(75) Inventors: Véronique Gillon, Essey-les-Nancy (FR); Philippe Moussou, Tomblaine (FR); Jean-Luc Contet-Audonneau, Saint-Max (FR); Olga Freis, Seichamps (FR)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/328,684

(22) Filed: Dec. 16, 2011

(65) Prior Publication Data

US 2012/0129784 A1 May 24, 2012

Related U.S. Application Data

(63) Continuation of application No. 12/092,476, filed as application No. PCT/EP2006/010258 on Oct. 25, 2006, now Pat. No. 8,101,574.

(30) Foreign Application Priority Data

Nov. 3, 2005 (EP) .................................... 05023954

(51) Int. Cl.
*A61K 38/00* (2006.01)
*A61P 17/00* (2006.01)
*A61P 25/04* (2006.01)

(52) U.S. Cl. ..................................... 514/18.8; 514/18.4
(58) Field of Classification Search .................... None
See application file for complete search history.

(56) References Cited

U.S. PATENT DOCUMENTS

| | | | |
|---|---|---|---|
| 4,172,887 A | 10/1979 | Vanlerberghe et al. | |
| 4,350,627 A | 9/1982 | de Castiglione et al. | |
| 4,966,848 A | 10/1990 | Smith et al. | |
| 5,223,421 A | 6/1993 | Smith et al. | |
| 5,702,688 A | 12/1997 | Yu et al. | |
| 5,763,576 A | 6/1998 | Powers | |
| 5,837,218 A | 11/1998 | Peers et al. | |
| 5,885,958 A | 3/1999 | Zadina et al. | |
| 6,048,902 A | 4/2000 | Lebwohl et al. | |
| 8,101,574 B2* | 1/2012 | Gillon et al. ................ | 514/18.8 |
| 2003/0204063 A1 | 10/2003 | Gravel et al. | |
| 2007/0060527 A1 | 3/2007 | Fogelman et al. | |
| 2009/0311184 A1* | 12/2009 | Yu .................................. | 424/9.1 |
| 2011/0287040 A1* | 11/2011 | Maione et al. ............ | 424/185.1 |
| 2012/0156279 A1* | 6/2012 | Yu et al. ....................... | 424/449 |

FOREIGN PATENT DOCUMENTS

| | | |
|---|---|---|
| DE | 19756377 | 6/1999 |
| DE | 10 2009 002 286 | 2/2010 |
| FR | 2252840 | 6/1975 |
| JP | 62 099315 | 10/1987 |
| JP | 2004-175687 A | 6/2004 |
| PL | 189753 | 9/2005 |
| WO | WO-95/22557 | 8/1995 |
| WO | WO-97/07130 | 2/1997 |
| WO | WO-98/42732 | 10/1998 |
| WO | WO-03/020304 | 3/2003 |
| WO | WO-2006/026780 | 3/2006 |

OTHER PUBLICATIONS

Kosmetik-verordnung, Appendix 6, Parts A and B, Deutsches Institut fur Korperpflege und Hygiene e.V.
Kosmetische Faerbemittel, Farbstoffkommission der Deutschen Forschungsgemeinschaft, Verlag Chemie, Weinheim 1984, 81-106.
Non-Final Office Action in U.S. Appl. No. 12/092,476, mailed Mar. 31, 2011, 20 pgs.
Chavigny, Caroline, "Sensitive skin: The quest for comfort", *Parfume Cosmetiques Actualites*, vol. 178 2004, 128, 130, 132-138, 141-143, 145, 146, 148, 150, 152, 154, 156, 158, 160, 162, 164, 167-169.
Lochhead, R. Y. et al., "Encyclopedia of Polymers and Thickeners for Cosmetics", *Cosmetics & Toiletries*, 108 1993, 95-135.

\* cited by examiner

*Primary Examiner* — Marcela M Cordero Garcia
(74) *Attorney, Agent, or Firm* — Servilla Whitney LLC

(57) ABSTRACT

Oligopeptides according to formula (I) and/or (II), $R_1$-Tyr-Pro-Trp-Phe-$NH_2$ (I, SEQ ID NO:1); $R_1$-Tyr-Pro-PhePhe-$NH_2$ (II, SEQ ID NO:2), wherein $R_1$ is linked to the $NH_2$-group of the amino-terminal part of Tyr and is selected from the group consisting of —H; a linear saturated or unsaturated or branched saturated or unsaturated acyl group having 1 to 24 carbon atoms, which may be functionalized by a —OH, —SH, —COOH or —CONH+ group; a sterol or a sphingolipid group which is linked to the amino terminal part of Tyr via a bifunctional linker are disclosed. Cosmetic compositions containing the oligopeptides are also disclosed.

20 Claims, No Drawings

OLIGOPEPTIDES AND COSMETIC COMPOSITIONS CONTAINING THE OLIGOPEPTIDES

CROSS REFERENCE TO RELATED APPLICATIONS

This application is a continuation of U.S. Ser. No. 12/092,476, filed May 2, 2008, now U.S. Pat. No. 8,101,574 which is a National Stage Entry of PCT/EP2006/010258, filed Oct. 25, 2006, and claims priority under 35 U.S.C. Section 119 of European Patent Application No. EP05023954.0 filed Nov. 3, 2005, the contents of which are incorporated by reference herein in their entireties.

REFERENCE TO SEQUENCE LISTING

The computer readable form of the Sequence Listing identified as "40163USA_ST25.txt" (1.74 KB), created on Dec. 26, 2010, and filed in parent application U.S. Ser. No. 12/092,476 on Dec. 26, 2010, is hereby incorporated by reference.

FIELD OF THE INVENTION

The present invention relates to the cosmetic use of oligopeptides, among them endomorphin-1 and endomorphin-2, cosmetic compositions which comprise such oligopeptides as well as certain oligopeptide derivatives themselves.

BACKGROUND OF THE INVENTION

Cosmetic preparations are available nowadays to the consumer in a large number of combinations. In this regard, it is not only expected that these cosmetics exhibit a particular care effect or overcome a certain deficiency, but there is an evermore frequent requirement for products which have several properties at the same time and thus exhibit an improved performance spectrum. Of particular interest are substances which both favorably influence the technical properties of the cosmetic product, such as storage stability, photostability and ability to be formulated, and also at the same time constitute active ingredients which confer care, irritation-suppressing and/or photoprotective properties for skin and/or hair for example. Especially, good skin compatibility and particularly good skin compatibility for humans with sensitive skin is of increasing importance.

Sensitive skin is a condition of subjective cutaneous hyperactivity to environmental factors or stimuli. Approximately 40% of the population considers themselves to possess the characteristics of sensitive skin. Consumers who perceive their skin as sensitive report exaggerated reactions when their skin is in contact with cosmetics, soaps and sunscreens, and worsening after exposure to dry, cold or wind climate, to sun or UV irradiation, to polluted environment, to physical treatments as depilation, shaving, or to stress. They react with subjective symptoms like itching, burning, stinging, prickling or tingling.

Mechanistic aspects of sensitive skin are still unclear, but an increased permeability of the stratum corneum and acceleration of the nerve response in skin are considered to be involved.

Various literature papers address the cosmetic treatment of sensitive skin. In Parfums Cosmetiques Actualités, 2004, 178, 128-169, C. Chavigny reviewed the different strategy and products to increase the skin tolerance threshold, via restoration of the cutaneous barrier and via limiting the production of the cellular mediators involved in the inflammatory reaction.

The peptides endomorphin-1 (H-Tyr-Pro-Trp-Phe-NH$_2$) (SEQ ID NO:5) and endomorphin-2 (H-Tyr-Pro-Phe-Phe-NH$_2$) (SEQ ID NO:6) are known pharmaceutical agents.

WO 98/42732 (EP 0 994 897) discloses the peptides endomorphine-1 (H-Tyr-Pro-Trp-Phe-NH$_2$) (SEQ ID NO:5) and endomorphine-2 (H-Tyr-Pro-Phe-Phe-NH$_2$) (SEQ ID NO:6) and several structural variations and their use in pharmaceutical compositions. No cosmetic use is described. No synthetic variants (acetylated forms) are disclosed.

WO 03/020304 (EP1427438) describes pharmaceutical compositions comprising an endomorphin for use in the treatment or prophylaxis of inflammation as well as autoimmune disorders such as rheumatoid arthritis, systemic lupus erythematosus, multiple sclerosis, psoriasis or asthma. The endomorphin is selected from natural endomorphins, synthetic endomorphins, endomorphin analogues, endomorphin mimetics, functional fragments of natural endomorphins, functional fragments of synthetic endomorphins and endomorphin derivatives. In a preferred embodiment, endomorphin-1 or endomorphin-2 are used. The endomorphin derivatives described are such that are obtained by glycosylation, sulphation or hydroxylation or "any other known modification method for peptides." The peptide derivatives of the present invention are not disclosed nor their cosmetic use.

WO 97/07130 (EP 845003 B1) describes tetra-peptides and tetra-peptide derivatives and their pharmaceutical use in the treatment of pain. The tetra-peptide always contains either D-Ala or D-Arg. WO 95122557 discloses oligopeptides, among them endomorphine-2 and their pharmaceutical use in the treatment of pain. U.S. Pat. No. 4,350,627 discloses a variety of tetra and penta-peptides and their therapeutic use.

The object of the present invention was to provide cosmetic compositions which are suitably to be used by humans with sensitive skin. In a further object of the invention, the cosmetic compositions should not only prevent subjective symptoms of sensitive skin like itching, burning, stinging, prickling or tingling but should also ameliorate existing symptoms of sensitive skin. It was a further objective of the invention to provide cosmetic compositions which help relieve sensitive skin in decreasing subjective cutaneous hyperactivity to environmental factors or stimuli and attenuating corresponding skin subjective symptoms like itching, burning, stinging, prickling or tingling. It was a further objective of the invention to provide cosmetic preparations which allow the incorporation of known irritating agents such as e.g. alpha-hydroxyl acids or retinol, in cosmetic preparations with the goal to obtain non-irritating compositions, which can thus be safely applied by humans with sensitive skin.

In addition, the cosmetic formulations should be preferably non-toxic and compatible with the most common cosmetic ingredients.

Surprisingly, it has now been found that oligopeptides according to the invention satisfy the needs described above.

None of the documents of the prior art describe oligopeptides of the invention nor the cosmetic use of the claimed oligopeptides. None of the documents describes oligopeptides which can be used on sensitive skin.

BRIEF SUMMARY OF THE INVENTION

The present invention is directed to a composition suitable for use in cosmetic applications, which composition comprises an oligopeptide according to formula (I) and/or (II) of:

(SEQ ID NO: 1)
R$_1$-Tyr-Pro-Trp-Phe-NH$_2$ (I)

-continued

R₁-Tyr-Pro-Phe-Phe-NH₂ (II)    (SEQ ID NO: 2)

wherein $R_1$ is linked to the $NH_2$-group of the amino-terminal portion of Tyr and is selected from the group consisting of:
 a) —H;
 b) a linear saturated or unsaturated or branched saturated or unsaturated acyl group having 1 to 24 carbon atoms, which acyl group can be functionalized by a —OH, —SH, —COOH or —CONH₂ group; and
 c) a sterol or a sphingolipid group which is linked to the amino terminal portion of Tyr by a bifunctional linker.

Accordingly, the invention is directed to the cosmetic use of oligopeptides according to SEQ ID NO:1 and/or SEQ ID NO:2, wherein $R_1$ has the above-described meaning.

It has been found that the oligopeptides according to the invention possess good cosmetic properties due to their soothing and caressing properties.

It has also been found that the oligopeptides according to the invention are suitable for the preparation of compositions for treating sensitive skin.

Thus, another aspect of the present invention is a cosmetic composition which comprises:
 1) an oligopeptide according to formula (I) and/or (II) of:

R₁-Tyr-Pro-Trp-Phe-NH₂ (I)    (SEQ ID NO: 1)

R₁-Tyr-Pro-Phe-Phe-NH₂ (II)    (SEQ ID NO: 2)

wherein $R_1$ is linked to the $NH_2$-group of the amino-terminal portion of Tyr and is selected from the group consisting of:
 a) —H;
 b) a linear saturated or unsaturated or branched saturated or unsaturated acyl group having 1 to 24 carbon atoms, which acyl group can be functionalized by a —OH, —SH, —COOH or —CONH₂ group; and
 c) a sterol or a sphingolipid group which is linked to the amino terminal portion of Tyr by a bifunctional linker;
 2) a cosmetic agent; and
 3) optionally, an additive or auxiliary suitable for use in a cosmetic composition.

It has also been found that the oligopeptides according to the invention can be used in cosmetic compositions which contain known irritating cosmetic agents. Surprisingly, it has been found that the irritating potential of these known irritating cosmetic agents is reduced by the oligopeplides according to the invention.

Thus, a further embodiment of the invention is directed to cosmetic compositions comprising at least one oligopeptide according to formula (I) and/or formula (II) and at least one cosmetic agent selected from the group consisting of alpha-hydroxy acids, beta-hydroxy acids and retinoids.

DETAILED DESCRIPTION OF THE INVENTION

Cosmetic Agent

The cosmetic agent can be an alpha-hydroxy acid. Suitable is any cosmetically acceptable alphahydroxy acid, salts thereof and esters thereof. Preferably, alpha-hydroxy acids are chosen wherein the alpha-hydroxy acid is selected from C2 to C12 alpha hydroxyl acids and salts thereof and esters thereof with a C2 to C24, preferably C14 to C22 alcohol.

The cosmetic agent can be a beta-hydroxy acid. Suitable is any cosmetically acceptable beta-hydroxy acid, salts thereof and esters thereof. Preferably, beta-hydroxy acids are chosen wherein the beta-hydroxy acid is selected from C2 to C12 beta-hydroxyl acids and salts thereof and esters thereof with a C2 to C24, preferably C14 to C22 alcohol.

In a preferred embodiment of the invention, the alpha-hydroxy or beta-hydroxy acid or salt or ester thereof is used, wherein the acid is preferably chosen from the group consisting of lactic acid, citric acid, glycolic acid, gentisic acid, salicylic acid, gluconic acid and heptonic acid.

The cosmetic agent can be a retinoid. Suitable retinoids according to the invention can be chosen from the group consisting of retinol, retinal, retinoic acid, retinyl acetate, retinyl palmitate and retinyl ascorbate.

R1 moiety

The amino-terminal part of Tyr is linked via Rt. Rt is selected from the group consisting of:
 a) —H
 b) a linear saturated or unsaturated or branched saturated or unsaturated acyl group having 1 to 24 carbon atoms, which may be funclionalized by a —OH, —SH, —COOH or —CONH₂ group, or
 c) a sterol or a sphingolipid group which is linked to the amino terminal part of Tyr via a bifunctional linker.

In one embodiment, the amino terminal is not substituted but consists of an amino group. It is within the scope of the invention that, in case $R_1$=H, the oligopeptide of the invention can be protonated, and be present as salt, e.g. as chloride, bromide, fluoride or iodide.

In a preferred embodiment, the oligopeptide according to the invention is endomorphin-1 [Tyr-ProTrp-Phe-NH₂] (SEQ ID NO:5) and/or endomorphin-2 [Tyr-Pro-Phe-Phe-NH₂] (SEQ ID NO:6).

In a preferred embodiment of the invention, R1 is a linear saturated or unsaturated or branched saturated or unsaturated acyl group having 1 to 24 carbon atoms, having 1 to 4, preferably 1 to 6, preferably 1 to 12, preferably 10 to 20, more preferably 12 to 18 carbon atoms. In one embodiment of the invention, the acyl group has $\leq 12$, $\leq 11$, $\leq 10$, $\leq 9$, $\leq 8$, $\leq 7$, $\leq 6$, $\leq 5$, $\leq 4$, $\leq 3$, $\leq 2$ carbon atoms.

The radical $R_1$ is preferably selected from the group which is formed by acetyl ($CH_3$—CO—), ethanoyl ($CH_3$—$CH_2$—CO—), propionyl, butanoyl (=butyryl; $CH_3$—$(CH_2)_2$—CO—), decanoyl, palmitoyl ($CH_3$—$(CH_2)_{14}$—CO—), stearoyl ($CH_3$—$(CH_2)_{16}$—CO—), oleyl, lipoyl, linoleyl or conjugated linoleyl; and particularly preferred is acetyl.

Thus, in an especially preferred embodiment of the invention, the oligopeptide according to formula (I) is N-Acetyl-Tyr-Pro-Trp-Phe-NH₂ (SEQ ID NO:3) and/or N-Acetyl-Tyr-Pro-Phe-Phe-NH₂ (SEQ ID NO:4).

In one embodiment of the invention, the acyl group can be further functionalized by one or more of the functional groups selected from the group consisting of —OH, —SH, —COOH and —CONH₂.

In one embodiment of the invention, $R_1$ is a sterol group. The sterol group can be selected from a plant sterol or from a sterol of animal origin.

Sterols in the context of the invention are steroids which only contain a hydroxyl group but no other functional groups at C-3. Formally, therefore, they are alcohols which is why this group of compounds is also referred to occasionally as sterols. In general, sterols contain from about 27 to about 30 carbon atoms and one double bond in the 5/6 position and occasionally in the 7/8, 8/9 or other positions. Sterols which may be used for the purposes of the invention are those obtained from natural products such as, for example, soya, rapeseed, sunflower, coconut, palm kernel and palm oil. Preferred sterols are sigmasterol, campesterol, sitosterol, brassicasterols, stigmasterol, D5 avenasterol, D7 avenasterol, ergosterol, citrostadienol, cholesterol, lanosterols, spongosterols, fungisterols, stellasterols, zymosterols and mixtures thereof and, more particularly, phytosterols based on ergosterols, avenasterols (D5 and D7 avenasterol}, campesterols, stigmasterols, sitosterols, brassicasterols, citrosdandiols, sigmastandiols and mixtures thereof. Any other phytosterol known to the expert may also be used.

In a preferred embodiment, the sterol group is selected from the group consisting of cholesterol, stigmasterol, sitosterol, or brassicasterol.

In another embodiment, $R_1$ is a sphingolipid, preferably selected from the group consisting of sphingosine, phytosphingosine, dehydrosphingosine or deshydrophytosphingosine.

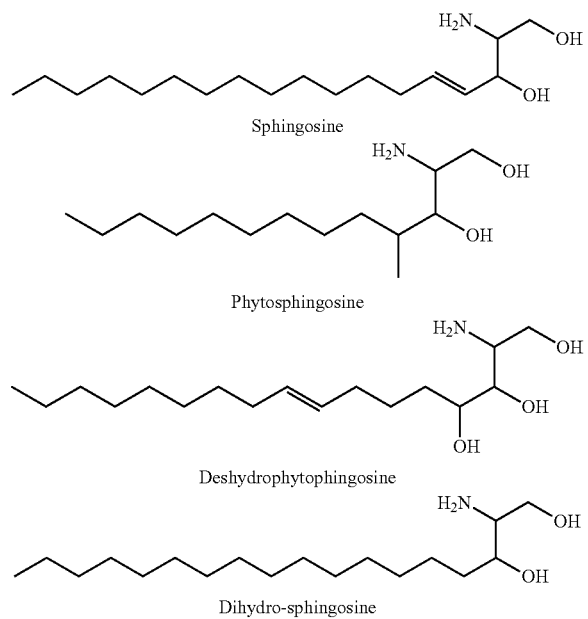

The sterol or the sphingolipid is linked to the oligopeptide using a bifunctional linker such as a diacid, for example succinic acid. The sterol hydroxyl group at C-3 can be linked via an ester bond to the bifunctional linker, which can be linked via an amide bond to the amino-terminal part of Tyr. The sphingolipid amino group at C-1 can be linked via an amide bond to the bifunctional linker, which can be linked via an amide bond to the amino-terminal part of Tyr.

The terms "oligopeptide" and "oligopeptides" are used synonymously to encompass single oligopeptide species of formula (I) and/or (II) as well as mixtures of at least 2, at least 3, or more oligopeptides according to formula (I) and/or (II) as well as mixtures of at least one single species of formula (I) with at least one single species of formula (II). In case where $R_1$ is not=H, the term "oligopeptide derivative" would be a more precise term. As used in this description, the term "oligopeptide" or "oligopeptides" encompasses oligopeptides as well as oligopeptide derivatives, as well as salts of the oligopelides and of the oligopeptide derivatives. Such suitable salts include sodium- or potassium-salts.

The amino acids can either occur in the L, the D, or the DL form in the peptide fragment. In a preferred embodiment of the invention, the amino acids are all in L form.

Synthesis of Oligopeptides

The oligogpeptides according to the invention can be obtained by chemical or enzymatic synthesis. They can also be obtained by controlled hydrolysis of natural proteins of microorganisms, plants or animals which contain the oligopeptides or precursors of the oligopeptides (e.g. endomorphine-1 or endomorphine-2) according to the invention.

The either chemically or enzymatically obtained endomorphine-1 or endomorphine-2 can then be further derivatized (e.g. acetylated) by known chemical or enzymatic techniques to obtain the oligopeptides according to the invention.

The oligopeptides can also be produced by microorganisms, which either naturally form the oligopeptides, or have possibly been genetically modified or are manipulated in some other way during fermentation through fermentation conditions such that they form the oligopeptides according to the invention.

In case the oligopeptides (or their precursors) are obtained by hydrolysis of proteins, the thus obtained oligopeptides may be used crude, or may be further purified by known techniques (membrane filtration, chromatography, immuneprecipitation) to obtain the desired oligopeptides.

Cosmetic Compositions Comprising Oligopeptides

Another embodiment of the invention is directed to cosmetic compositions comprising at least one oligopeptide according to formula (I) and/or (II).

The oligopeptides are preferably used in a concentration of from about 0.001 to 1000 ppm, preferably 0.05 to 500 ppm, more preferably from 0.5 to 100 ppm.

The oligopeptides are preferably dissolved or solubilized in one or more solvents which are approved for cosmetic preparations, such as, for example, water, glycerol, propylene glycol, butylene glycol, pentylene glycol, ethoxylated or propoxylated diglycols, ethanol, propanol, isopropanol or mixtures of said solvents. Furthermore, it is possible to use the oligopeptides solubilized in liposomes or adsorbed to organic polymers, or mineral supports or similar material which is acceptable for topical application.

Besides the solvents, further auxiliaries and additives may also be present in the preparations which are used according to the invention.

Cosmetic Compositions

The oligopeptides and the cosmetic uses according to the invention are suitable for use in making cosmetic compositions, such as, for example, hair shampoos, hair lotions, foam baths, shower baths, creams, gels, lotions, alcoholic and aqueous/alcoholic solutions, emulsions, wax/fat masses, stick preparations, powders or ointments. These compositions can also comprise, as further auxiliaries and additives, mild surfactants, oil bodies, emulsifiers, pearlescent waxes, consistency regulators, thickeners, superfatting agents, stabilizers, polymers, silicone compounds, fats, waxes, lecithins, phospholipids, UV photoprotective factors, biogenic active ingredients, antioxidants, deodorants, antiperspirants, antidandruff agents, film formers, swelling agents, insect repellents, self-tanning agents, tyrosine inhibitors (depigmentation agents), hydrotropes, solubilizers, preservatives, perfume oils, dyes and the like.

Surfactants

Surface-active substances which may be present are anionic, nonionic, cationic and/or amphoteric or zwitterionic surfactants, the content of which in the compositions is usually about 1 to 70% by weight, preferably 5 to 50% by weight and in particular 10 to 30% by weight.

Typical examples of anionic surfactants are soaps, alkylbenzenesulphonates, alkanesulphonates, olefinsulphonates, alkyl ether sulphonates, glycerol ether sulphonates, α-methyl ester sulphonates, sulpho fatty acids, alkyl sulphates, alkyl ether sulphates, glycerol ether sulphates, fatty acid ether sulphates, hydroxyl mixed ether sulphates, monoglyceride (ether) sulphates, fatty acid amide (ether) sulphates, mono- and dialkyl sulphosuccinates, mono- and dialkyl sulphosuccinamates, sulphotriglycerides, amide soaps, ether carboxylic acids and salts thereof, fatty acid isethionates, fatty acid sarcosinates, fatty acid taurides, N-acylaminoacids, such as, for example, acyl lactylates, acyl tartrates, acyl glutamates and acyl aspartates, alkyl oligoglucoside sulphates, protein fatty acid condensates (in particular wheat-based vegetable products) and alkyl(ether) phosphates. If the anionic surfactants comprise polyglycol ether chains, these can have a conventional homologue distribution, but preferably have a narrowed homologue distribution.

Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partially oxidized alk(en)yl oligoglycosides and glucoronic acid derivatives, fatty acid N-alkylglucamides, protein hydrolysates (in particular wheat-based vegetable products), polyol fatty acid esters, sugar esters, sorbitan esters, polysorbates and amine oxides. If the nonionic sulfactants contain polyglycol ether chains, these can have a conventional homologue distribution, but preferably have a narrowed homologue distribution.

Typical examples of cationic surfactants are quaternary ammonium compounds, such as, for example, dimethyldistearylammonium chloride, and ester quats, in particular quaternized fatty acid trialkanolamine ester salts.

Typical examples of amphoteric and zwitterionic surfactants are alkylbetaines, alkylamidobetaines, aminopropionates, aminoglycinates, imidazoliniumbetaines and sulphobetaines. The specified surfactants are exclusively known compounds.

Typical examples of particularly suitable mild, i.e. particularly skin-compatible, surfactants are fatty alcohol polyglycol ether sulphates, monoglyceride sulphates, mono- and/or dialkyl sulphosuccinates, fatty acid isethionates, fatty acid sarcosinates, fatty acid taurides, fatty acid glutamates, α-olefinsulphonates, ether carboxylic acids, alkyl oligoglucosides, fatty acid glucamides, alkylamidobetaines, amphoacetals and/or protein fatty acid condensates, the latter preferably being based on wheat proteins.

Oil Bodies

Suitable oil bodies are, for example, Guerbet alcohols based on fatty alcohols having 6 to 18, preferably 8 to 0, carbon atoms, esters of linear $C_6$-$C_{22}$-fatty acids with linear or branched $C_6$-$C_{22}$-fatty alcohols and/or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxycarboxylic acids with linear or branched $C_6$-$C_{22}$-fatty alcohols (cf. DE 19756377 A1), in particular dioctyl malates, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, dicaprylyl carbonate (Cetiol® CC), Guerbet carbonates based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or unsymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicon methicone types, inter alia) and/or aliphatic or naphthenic hydrocarbons, such as, for example, squalane, squalene or dialkylcyclohexanes.

Emulsifiers

Suitable emulsifiers are, for example, nonionic surfactants from at least one of the following groups:

addition products of from 2 to 30 mol of ethylene oxide and/or 0 to 5 mol of propylene oxide to linear fatty alcohols having 8 to 22 carbon atoms, to fatty acids having 12 to 22 carbon atoms, to alkylphenols having 8 to 15 carbon atoms in the alkyl group, and alkylamines having 8 to 22 carbon atoms in the alkyl radical;

alkyl and/or alkenyl oligoglycosides having 8 to 22 carbon atoms in the alk(en)yl radical and the ethoxylated analogues thereof;

addition products of from 1 to 15 mol of ethylene oxide to castor oil and/or hydrogenated castor oil;

addition products of from 15 to 60 mol of ethylene oxide to castor oil and/or hydrogenated castor oil;

partial esters of glycerol and/or sorbitan with unsaturated, linear or saturated, branched fatty acids having 12 to 22 carbon atoms and/or hydroxycarboxylic acids having 3 to 18 carbon atoms, and the ad ducts thereof with 1 to 30 mol of ethylene oxide;

partial esters of polyglycerol (average degree of self-condensation 2 to 8), polyethylene glycol (molecular weight 400 to 5 000), trimethylolpropane, pentaerythritol, sugar alcohols (e.g. sorbitol), alkyl glucosides (e.g. methyl glucoside, butyl glucoside, laury! glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 mol of ethylene oxide;

mixed esters of pentaerythritol, fatty acids, citric acid and fatty alcohol and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof;

wool wax alcohols;

polysiloxane-polyalkyl-polyether copolymers and corresponding derivatives;

block copolymers, e.g. polyethylene glycol-30 dipolyhydroxystearates;

polymer emulsifiers, e.g. Pemulen grades (TR-1, TR-2) from Goodrich;

polyalkylene glycols, and glycerol carbonate.

Ethylene Oxide Addition Products

The addition products of ethylene oxide and/or of propylene oxide to fatty alcohols, fatty acids, alkylphenols or to castor oil are known, commercially available products. These are homologue mixtures whose average degree of alkoxylation corresponds to the ratio of the amounts of substance of ethylene oxide and/or propylene oxide and substrate with which the addition reaction is carried out. C1211a-fatty acid mono- and diesters of addition products of ethylene oxide to glycerol are known as refatting agents for cosmetic preparations.

Alkyl and/or Alkenyl Oligoglycosides

Alkyl and/or alkenyl oligoglycosides, their preparation and their use are known from the prior art. They are prepared, in particular, by reacting glucose or oligosaccharides with primary, alcohols having 8 to 18 carbon atoms. With regard to the glycoside radical, both monoglycosides, in which a cyclic sugar radical is glycosidically bonded to the fatty alcohol, and also oligomeric glycosides having a degree of oligomerization of up to, preferably, about 8, are suitable. The degree of oligomerization here is a statistical average value which is based on a homologue distribution customary for such technical-grade products.

Partial Glycerides

Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride, and the technical-grade mixtures thereof which may also comprise small amounts of triglyceride as a minor product of the preparation process. Likewise suitable are addition products of 1 to 30 mol, preferably 5 to 10 mol, of ethylene oxide to said partial glycerides.

Sorbitan Esters

Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, 10 sorbitan trierucate, sorbitan monoricinoleate, sorbitan sesquiricinoleate, sorbitan diricinoleate, sorbitan triricinoleate, sorbitan mono hydroxystearate, sorbitan sesquihydroxystearate, sorbitan di hydroxystearate, sorbitan tri hydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate, and technical-grade mixtures thereof. Likewise suitable are addition products of from 1 to 30 mol, preferably 5 to 10 mol, of ethylene oxide to said sorbitan esters.

Polyglycerol Esters

Typical examples of suitable polyglycerol esters are polyglyceryl-2 dipolyhydroxystearate (Dehymuls® PGPH), polyglycerol-3 diisostearate (Lameform® TGI}, polyglyceryl-4 isostearate (Isolan® GI34), polyglyceryl-3 oleate, diisostearoyl polyglyceryl-3 diisostearate (Isolan® PDI), polyglyceryl-3 methylglucose distearate (Tego Care® 450), polyglyceryl-3 beeswax (Cera Bellina®), polyglyceryl-4 caprate (Polyglycerol Caprate T2010/90), polyglyceryl-3 cetyl ether (Chimexane® NL), polyglyceryl-3 distearate (Cremophor$_{cc}$>GS 32) and polyglyceryl polyricinoleate (AdmuJ® WOL 1403), polyglyceryl dimerate isostearate, and mixtures thereof. Examples of further suitable polyol esters are the mono-, di- and triesters, optionally reacted with 1 to 30 mol of ethylene oxide, of trimethylolpropane or pentaerythritol with lauric acid, coconut fatty acid, tallow fatty acid, palmitic acid, stearic acid, oleic acid, behenic acid and the like.

Anionic Emulsifiers

Typical anionic emulsifiers are aliphatic fatty acids having 12 to 22 carbon atoms, such as, for example, palmitic acid, stearic acid or behenic acid, and dicarboxylic acids having 12 to 22 carbon atoms, such as, for example, azelaic acid or sebacic acid.

Amphoteric and Cationic Emulsifiers

Furthermore, zwitterionic surfactants can be used as emulsifiers. The term "zwitterionic surfactants" refers to those surface-active compounds which carry at least one quaternary ammonium group and at least one carboxylate and one sulphonate group in the molecule. Particularly suitable zwitterionic surfactants are the so-called betaines, such as N-alkyl-N,N-dimethylammonium glycinates, for example cocoalkyldimethylammonium glycinates, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethylcarboxymethyl glycinate. Particular preference is given to the fatty acid amide derivative known under the CTFA name Cocamidopropy/Betaine. Likewise suitable emulsifiers are ampholytic surfactants. The term "ampholytic surfactants" means those surface-active compounds which, apart from a $C_{8/18}$-alkyl or -acyl group, contain at least one free amino group and at least one —COOH or —SO$_3$H group in the molecule and are capable of forming internal salts. Examples of suitable ampholytic surfactants are N-alkylglycines, N-alkylaminopropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkyl aminoacetic acids having in each case about 8 to 18 carbon atoms in the alkyl group. Particularly preferred ampholytic surfactants are N-cocoalkylaminopropionate, cocoacylaminoethylaminopropionate and $C_{12/18}$-acylsarcosine. Finally, cationic surfactants are also suitable as emulsifiers, those of the ester quat type, preferably methyl-quaternized difatty acid triethanolamine ester salts, being particularly preferred.

Fats and Waxes

Typical examples of fats are glycerides, i.e. solid or liquid vegetable or animal products which consist essentially of mixed glycerol esters of higher fatty acids, suitable waxes are inter alia natural waxes, such as, for example, candelilla wax, carnauba wax, Japan wax, esparto grass wax, cork wax, guaruma wax, rice germ oil wax, sugarcane wax, ouricury wax, montan wax, beeswax, shellac wax, spermaceti, lanolin (wool wax), uropygial grease, ceresin, ozokerite (earth wax), petrolatum, paraffin waxes, microcrystalline waxes; chemically modified waxes (hard waxes), such as, for example, montan ester waxes, sasol waxes, hydrogenated jojoba waxes, and synthetic waxes, such as, for example, polyalkylene waxes and polyethylene glycol waxes. In addition to the fats, suitable additives are also fat-like substances, such as lecithins and phospholipids. The term lecithins is understood by the person skilled in the art as meaning those glycerophospholipids which are founded from fatty acids, glycerol, phosphoric acid and choline by esterification. Lecithins are thus also often as phosphatidylcholines (PC) in the specialist world. Examples of natural lecithins which may be mentioned are the cephalins, which are also referred to as phosphatidic acids and constitute derivatives of 1,2-diacyl-sn-glycerol-3-phosphoric acids. By contrast, phospholipids are usually understood as meaning mono- and preferably diesters of phosphoric acid with glycerol (glycerol phosphates), which are generally classed as fats. In addition, sphingosines or sphingolipids are also suitable.

Pearlescent Waxes

Examples of suitable pearlescent waxes are: alkylene glycol esters, specifically ethylene glycol distearate; fatty acid alkanolamides, specifically coconut fatty acid diethanolamide; partial glycerides, specifically stearic acid monoglyceride; esters of polybasic, optionally hydroxysubstituted carboxylic acids with fatty alcohols having 6 to 22 carbon atoms, specifically long-chain esters of tartaric acid; fatty substances, such as, for example, fatty alcohols, fatty ketones, fatty aldehydes, fatty ethers and fatty carbonates, which have a total of at least 24 carbon atoms, specifically laurene and distearyl ether; fatty acids, such as stearic acid, hydroxystearic acid or behenic acid, ring-opening products of olefin epoxides having 12 to 22 carbon atoms with fatty alcohols having 12 to 22 calbon atoms and/or polyols having 2 to 15 carbon atoms and 2 to 10 hydroxyl groups, and mixtures thereof.

Consistency Regulators and Thickeners

Suitable consistency regulators are primarily fatty alcohols or hydroxy fatty alcohols having 12 to 22, and preferably 16 to 18, carbon atoms, and also partial glycerides, fatty acids or hydroxy fatty 5 acids. Preference is given to a combination of these substances with alkyl oligoglucosides and/or fatty acid N-methylglucamides of identical chain length and/or polyglycerol poly-12-hydroxystearates. Suitable thickeners are, for example, Aerosil grades (hydrophilic silicas), polysaccharides, in particular xanthan gum, guar guar, agar agar, alginates and tyloses, carboxymethylcellulose, hydroxyethylcellulose and hydroxypropylcellulose, and also relatively high molecular weight polyethylene glycol mono- and diesters of fatty acids, polyacrylates (e.g. Carbopols® and Pemulen grades from Goodrich; Synthalens® from Sigma; Keltrol grades from Kelco; Sepigel grades from Seppic; Salcare grades from Allied Colloids), polyacrylamides, polymers, polyvinyl alcohol and polyvinylpyrrolidone. Bentonites, such as, for example, Bentone® Gel VS 5PC (Rheox), which is a mixture of cyclopentasiloxane, disteardimonium hectorite and propylene carbonate, have also proven to be particularly effective. Also suitable are surfactants, such as, for example, ethoxylated fatty acid glycerides, esters of fatty acids with polyols such as, for example, pentaerythritol or trimethylolpropane, fatty alcohol ethoxylates having a narrowed homologue distribution or alkyl oligoglucosides, and electrolytes such as sodium chloride and ammonium chloride.

Superfatting Agents

Superfatting agents which can be used are substances such as, for example, lanolin and lecithin, and polyethoxylated or acylated lanolin and lecithin derivatives, polyol fatty acid esters, monoglycerides and fatty acid alkanolamides, the latter also serving as foam stabilizers.

Stabilizers

Stabilizers which can be used are metal salts of fatty acids, such as, for example, magnesium, aluminium and/or zinc stearate or ricinoleate.

Polymers

Suitable cationic polymers are, for example, cationic cellulose derivatives, such as, for example, a quaternized hydroxyethylcellulose obtainable under the name Polymer JR 400® from Amerchol, cationic starch, copolymers of diallylammonium salts and acrylamides, quaternized vinylpyrrolidone-vinylimidazole polymers, such as, for example, Luviquat® (BASF), condensation products of polyglycols and amines, quaternized collagen polypeptides, such as, for example, lauryldimonium hydroxypropyl hydrolyzed collagen (Lamequat®UGrGnau), quaternized wheat polypeptides, polyethyleneimine, cationic silicone polymers, such as, for example, amodimethicones, copolymers of adipic acid and dimethylaminohydroxypropyldiethylenetriamine (Cartaretim;®/Sandoz), copolymers of acrylic acid with dimethyldiallylammonium chloride (Merquat® 550/Chemviron), polyaminopolyamides, as described, for example, in FR 2252840 A, and crosslinked water-soluble polymers thereof, cationic chitin derivatives, such as, for example, quaternized chitosan, optionally in microcrystalline dispersion, condensation products from dihaloalkyls, such as, for example, dibromobutane with bisdialkylamines, such as, for example, bis-dimethylamino-1,3-propane, cationic guar gum, such as, for example, Jaguar® CBS, Jaguar® C-17, Jaguar® C-16 from Celanese, quaternized ammonium salt polymers, such as, for example, Mirapol® A-15, Mirapol® AD-1, Mirapol® AZ-1 from Miranol.

Suitable anionic, zwitterionic, amphoteric and nonionic polymers are, for example, vinyl acetate-crotonic acid copolymers, vinylpyrrolidone-vinyl acrylate copolymers, vinyl acetate-butyl maleate-isobornyl acrylate copolymers, methyl vinyl ether-maleic anhydride copolymers and esters thereof, uncrosslinked polyacrylic acids and polyacrylic acids crosslinked with polyols, acrylamidopropyltrimethylammonium chloride-acrylate copolymers, octylacrylamide-methyl methacrylate-tertbutylaminoethyl methacrylate-2-hydroxypropyl methacrylate copolymers, polyvinylpyrrolidone, vinylpyrrolidone-vinyl acetate copolymers, vinylpyrrolidone-dimethylaminoethyl methacrylatevinylcaprolactam terpolymers, and optionally derivatized cellulose ethers and silicones.

Silicone Compounds

Suitable silicone compounds are, for example, dimethylpolysiloxanes, methylphenylpolysiloxanes, cyclic silicones, and amino-, fatty acid-, alcohol-, polyether-, epoxy-, fluorine-, glycoside- and/or alkyl-modified silicone compounds, which can either be liquid or in resin form at room temperature. Also suitable are simethicones, which are mixtures of dimethicones having an average chain length of from 200 to 300 dimethylsiloxane units and hydrogenated silicates.

UV Photoprotective Filters

UV photo protective factors are, for example, to be understood as meaning organic substances (photoprotective filters) which are liquid or crystalline at room temperature and which are able to absorb ultraviolet rays and give off the absorbed energy again in the form of longer-wavelength radiation, e.g. heat. UVB filters can be oil-soluble or water-soluble. Examples of oil-soluble substances are:
    3-benzylidenecamphor or 3-benzylidenenorcamphor and derivatives thereof, e.g. 3-(4-methylbenzylidene)camphor;
    4-aminobenzoic acid derivatives, preferably 2-ethylhexyl-4-(dimethylamino)benzoate, 2-octyl-4-(dimethylamino)benzoate and amyl 4-(dimethylamino)benzoate;
    esters of cinnamic acid, preferably 2-ethylhexyl-4-methoxycinnamate, propyl 4-methoxycinnamate, isoamyl 4-methoxycinnamate, 2-ethylhexyl 2-cyano-3,3-phenylcinnamate (octocrylene);

esters of salicylic acid, preferably 2-ethylhexyl salicylate, 4-isopropylbenzyl salicylate, homomethyl salicylate;

derivatives of benzophenone, preferably 2-hydroxy-4-methoxybenzophenone, 2-hydroxy-4-methoxy-4'-methylbenzophenone, 2,2'-dihydroxy-4-methoxybenzophenone;

esters of benzalmalonic acid, preferably di-2-ethylhexyl-4-methoxybenzalmalonate;

triazine derivatives, such as, for example, 2,4,6-trianilino (p-carbo-2'-ethyl-1'-hexyloxy)-1,3,5-triazine and octyltriazone or dioctylbutamidotriazone (Uvasorb® HEB);

propane-1,3-diones, such as, for example, 1-(4-tert-butylphenyl)-3-(4'-methoxyphenyl)propane-1,3-dione;

ketotricyclo(5.2.1.0)decane derivatives.

Suitable water-soluble substances are:

2-phenylbenzimidazole-5-sulphonic acid and the alkali metal, alkaline earth metal, ammonium, alkylammonium, alkanolammonium and glucammonium salts thereof;

sulphonic acid derivatives of benzophenones, preferably 2-hydroxy-4-methoxybenzophenone-5 5-sulphonic acid and its salts;

sulphonic acid derivatives of 3-benzylidenecamphor, such as, for example, 4-(2-oxo-3-bornylidenemethyl)benzenesulphonic acid and 2-methyl-5-(2-oxo-3-bornylidene)sulphonic acid and salts thereof.

Suitable typical UV-A filters are, in particular, derivatives of benzoylmethane, such as, for example, 1-(4'-tert-butylphenyl)-3-(4'-methoxyphenyl)propane-1,3-dione, 4-tert-butyl-4'methoxydibenzoylmethane (Parsol® 1789), 1-phenyl-3-(4'-isopropylphenyl)propane-1,3-dione, and enamine compounds. The UV-A and UV-8 filters can of course also be used in mixtures. Particularly favourable combinations consist of the derivatives of benzoylmethane, e.g. 4-tert-butyl-4'-methoxydibenzoylmethane (Parsol® 1789) and 2-ethylhexyl -cyano-3,3-phenylcinnamate (octocrylene) in combination with esters of cinnamic acid, preferably 2-ethylhexyl 4-methoxycinnamate and/or propyl 4-methoxycinnamate and/or isoamyl 4-methoxycinnamate. Advantageously, such combinations are combined with water-soluble filters such as, for example, 2-phenylbenzimidazole-5-sulphonic acid and their alkali metal, alkaline earth metal, ammonium, alkylammonium, alkanolammonium and glucammonium salts.

As well as said soluble substances, insoluble light protection pigments, namely finely dispersed metal oxides or salts, are also suitable for this purpose. Examples of suitable metal oxides are, in particular, zinc oxide and titanium dioxide and also oxides of iron, zirconium, silicon, manganese, aluminium and cerium, and mixtures thereof. Salts which may be used are silicates (talc), barium sulphate or zinc stearate. The oxides and salts are used in the form of the pigments for skincare and skin-protective emulsions and decorative cosmetics. The particles here should have an average diameter of less than 100 nm, preferably between 5 and 50 nm and in particular between 15 and 30 nm. They can have a spherical shape, but it is also possible to use particles which have an ellipsoidal shape or a shape deviating in some other way from the spherical form. The pigments can also be surface-treated, i.e. hydrophilicized or hydrophobicized. Typical examples are coated titanium dioxides, such as, for example, titanium dioxide T 805 (Degussa) or Eusolex® T2000 (Merck). Suitable hydrophobic coating agents are here primarily silicones and, specifically in this case, trialkoxyoctylsilanes or simethicones. In sunscreens, preference is given to using so-called micro- or nanopigments. Preference is given to using micronized zinc oxide.

Biogenic Active Ingredients and Antioxidants

Biogenic active ingredients are understood as meaning, for example, tocopherol, tocopherol acetate, tocopherol palmitate, ascorbic acid, (deoxy)ribonucleic acid and fragmentation products thereof, p-glucans, retinol, bisabolol, allantoin, phytantriol, panthenol, AHA acids, amino acids, ceramides, pseudoceramides, essential oils, plant extracts, such as, for example, prunus extract, bambara nut extract and vitamin complexes.

Antioxidants interrupt the photochemical reaction chain which is triggered when UV radiation penetrates the skin. Typical examples thereof are amino acids {e.g. glycine, histidine, tyrosine, tryptophan) and derivatives thereof, imidazoles (e.g. urocanic acid) and derivatives thereof, peptides, such as D,L-carnosine, D-carnsine, L-carnosine and derivatives thereof (e.g. anserine), carotenoids, carotenes (e.g. a-carotene, ~-carotene, lycopene) and derivatives thereof, chlorogenic acid and derivatives thereof, lipoic acid and derivatives thereof (e.g. dihydrolipoic acid), auro-thioglucose, propylthiouracil and other thiols (e.g. thioredoxin, glutathione, cysteine, cystine, cystamine and the glycosyl, N-acetyl, methyl, ethyl, propyl, amyl, butyl and lauryl!, palmitoyl, oleyl, γ-linoleyl, cholesteryl and glyceryl esters thereof and salts thereof, dilauryl thiodipropionate, distearyl thiodipropionate, thiodipropionic acid and derivatives thereof (esters, ethers, peptides, lipids, nucleotides, nucleosides and salts), and sulphoximine compounds (e.g. buthionine sulphoximines, homocysteine sulphoximine, buthionine sulphones, penta-, hexa-, heptathionine sulphoximine) in very low tolerated doses (e.g. pmol to μmo/kg), and also (metal) chelating agents (e.g. a-hydroxy fatty acids, palmitic acid, phytic acid, lactoferrin), a-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of gum benzoin, rutic acid and derivatives thereof, α-glycosylrutin, ferulic acid, furfurylideneglucitol, carnosine, butylhydroxytoluene, butylhydroxy-anisole, nordihydroguaiacic acid, nordihydroguaiaretic acid, trihydroxybutyrophenone, uric acid and derivatives thereof, mannose and derivatives thereof, superoxide dismutase, zinc and derivatives thereof (e.g. ZnO, $ZnSO_4$) selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of said active ingredients which are suitable according to the invention.

Deodorants and Antimicrobial Agents

Cosmetic deodorants counteract, mask or remove body odors. Body odors arise as a result of the effect of skin bacteria on apocrine perspiration, with the formation of degradation products which have an unpleasant odor. Accordingly, deodorants comprise active ingredients which act as antimicrobial agents, enzyme inhibitors, odor absorbers or odor masking agents.

Antimicrobial Agents

Suitable antimicrobial agents are, in principle, all substances effective against gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxydiphenyl ether (triclosan), 4-chloro-3,5-dimethylphenol, 2,2'-methylenebis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynyl butylcarbamate, chlorhexidine, 3,4,4'-trichlorocarbanilide (TIC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, N-octylsalicylamide or N-decylsalicylamide.

Enzyme Inhibitors

Suitable enzyme inhibitors are, for example, esterase inhibitors. These are preferably trialkyl citrates, such as trimethyl citrate, tripropyl citrate, triisopropyl citrate, tributyl citrate and, in particular, triethyl citrate (Hydagen® CAT). The substances inhibit enzyme activity, thereby reducing the formation of odor. Other substances which are suitable esterase inhibitors are sterol sulphates or phosphates, such as, for example, lanosterol, cholesterol, campesterol, stigmasterol and sitosterol sulphate or phosphate, dicarboxylic acids and esters thereof, such as, for example, glutaric acid, monoethyl glutarate, diethyl glutarate, adipic acid, monoethyl adipate, diethyl adipate, malonic acid and diethyl malonate, hydroxycarboxylic acids and esters thereof, such as, for example, citric acid, malic acid, tartaric acid or diethyl tartrate, and zinc glycinate.

Odor Absorbers

Suitable odor absorbers are substances which are able to absorb and largely retain odor-forming compounds. They lower the partial pressure of the individual components, thus also reducing their rate of diffusion. It is important that in this process perfumes must remain unimpaired. Odor absorbers are not effective against bacteria. They comprise, for example, as main constituent, a complex zinc salt of ricinoleic acid or specific, largely odor-neutral fragrances which are known to the person skilled in the art as "fixatives•, such as, for example, extracts of labdanum or styrax or certain abietic acid derivatives. The odor masking agents are fragrances or perfume oils, which, in addition to their function as odor masking agents, give the deodorants their respective fragrance note. Perfume oils which may be mentioned are, for example, mixtures of natural and synthetic fragrances. Natural fragrances are extracts from flowers, stems and leaves, fruits, fruit peels, roots, woods, herbs and grasses, needles and branches, and resins and balsams. Also suitable are animal raw materials, such as, for example, civet and castoreum. Typical synthetic fragrance compounds are products of the ester, ether, aldehyde, ketone, alcohol and hydrocarbon type. Fragrance compounds of the ester type are, for example, benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, and the aldehydes include, for example, the linear alkanals having 8 to 18 carbon atoms, citral, citronellal, citronelly-loxyacetaldehyde, cyclamen aldehyde, hydroxycitronellal, lilial and bourgeonal, the ketones include, for example, the ion ones and methyl cedryl ketone, the alcohols include anethole, citronellol, eugenol, isoeugenol, geraniol, linalool, phenylethyl alcohol and terpineol, and the hydrocarbons include mainly the terpanes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden blossom oil, juniper berry oil, vetiver oil, olibanum oil, galbanum oil, labdanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evemyl, iraldein gamma, phenylacetic acid, geranyl acetate, benzyl acetate, rose oxide, romilat, irotyl and floramat alone or in mixtures.

Antiperspirants

Antiperspirants reduce the formation of perspiration by influencing the activity of the eccrine sweat glands, thus counteracting underarm wetness and body odor. Aqueous or anhydrous formulations of antiperspirants typically comprise the following ingredients:

astringent active ingredients,
oil components,
non ionic emulsifiers,
coemulsifiers,
consistency regulators,
auxiliaries, such as, for example, thickeners or complexing agents and/or
nonaqueous solvents, such as, for example, ethanol, propylene glycol and/or glycerol.

Suitable astringent antiperspirant active ingredients are primarily salts of aluminium, zirconium or of zinc. Such suitable antihydrotic active ingredients are, for example, aluminium chloride, aluminium chlorohydrate, aluminium dichlorohydrate, aluminium sesquichlorohydrate and complex compounds thereof, e.g. with 1,2-propylene glycol, aluminium hydroxyallantoinate, aluminium chloride tartrate, aluminium zirconium trichlorohydrate, aluminium zirconium tetrachlorohydrate, aluminium zirconium pentachlorohydrate and complex compounds thereof, e.g. with amino acids, such as glycine. In addition, customary oil-soluble and water-soluble auxiliaries may be present in antiperspirants in relatively small amounts. Such oil-soluble auxiliaries may, for example, be:

anti-inflammatory, skin-protective or perfumed essential oils,
synthetic skin-protective active ingredients and/or
oil-soluble perfume oils.

Customary water-soluble additives are, for example, preservatives, water-soluble fragrances, pH regulators, e.g. buffer mixtures, water-soluble thickeners, e.g. water-soluble natural or synthetic polymers, such as, for example, xanthan gum, hydroxyethylcellulose, polyvinylpyrrolidone or high molecular weight polyethylene oxides.

Film Formers

Customary film formers are, for example, chitosan, microcrystalline chitosan, quaternized chitosan, polyvinylpyrrolidone, vinylpyrrolidone-vinyl acetate copolymers, polymers of the acrylic acid series, quaternary cellulose derivatives, collagen, hyaluronic acid and salts thereof, and similar compounds.

Antidandruff Active Ingredients

Suitable antidandruff active ingredients are piroctone olamine (1-hydroxy-4-methyl-6-(2,4,4-trimythylpentyl)-2-(1H)-pyridinone manoethanolamine salt), BaypivaJ® (climbazole), Ketoconazole®, (4-acetyl-1-{-4-[2-(2,4-dichlorophenyl) r-2-(1H-imidazol-1-ylmethyl)-1,3-dioxylan-c-4-ylmethoxyphenyl}piperazine, ketoconazole, elubiol, selenium disulphide, sulphur colloidal, sulphur polyethylene glycol sorbitan monooleate, sulphur ricinole polyethoxylate, sulphur tar distillates, salicylic acid (or in combination with hexachlorophene), undecylenic acid monoethanolamide sulphosuccinate Na salt, Lamepon® UD (protein undecylenic acid condensate), zinc pyrithione, aluminium pyrithione and magnesium pyrithione/dipyrithione magnesium sulphate.

Swelling Agents

The swelling agents for aqueous phases may be montmorillonites, clay mineral substances, Pemulen, and alkyl-modified Carbopol grades (Goodrich). Other suitable polymers and swelling agents are given in the review by R. Lochhead in Cosm. Toil.108, 95 (1993).

Insect Repellents

Suitable insect repellents are N,N-diethyl-m-toluamide, 1,2-pentanediol or ethyl butylacetylaminopropionate.

Self-Tanning Agents and Depigmentation Agents

A suitable self-tanning agent is dihydroxyacetone. Suitable tyrosine inhibitors, which prevent the formation of melanin and are used in depigmentation agents, are, for example, arbutin, ferulic acid, kojic acid, coumaric acid and ascorbic acid (vitamin C).

Hydrotropic Agents

To improve the flow behavior, it is also possible to use hydrotropic agents, such as, for example, ethanol, isopropyl alcohol, or polyols. Polyols which are suitable here preferably have 2 to 15 carbon atoms and at least two hydroxyl groups. The polyols can also contain further functional groups, in particular amino groups, or be modified with nitrogen. Typical examples are glycerol;

alkylene glycols, such as, for example, ethylene glycol, diethylene glycol, propylene glycol, butylene glycol, hexylene glycol, and polyethylene glycols with an average molecular weight of from 100 to 1 000 daltons;

technical-grade oligoglycerol mixtures with a degree of self-condensation of from 1.5 to 10, such as, for example, technical-grade diglycerol mixtures with a diglycerol content of from 40 to 50% by weight;

methylol compounds, such as, in particular, trimethylolethane, trimethylolpropane, trimethylolbutane, pentaerythritol and dipentaerythritol;

lower alkyl glucosides, in particular those having 1 to 8 carbon atoms in the alkyl radical, such as, for example, methyl and butyl glucoside;

sugar alcohols having 5 to 12 carbon atoms, such as, for example, sorbitol or mannitol;

sugars having 5 to 12 carbon atoms, such as, for example, glucose or sucrose;

amino sugars, such as, for example, glucamine;

dialcohol amines, such as diethanolamine or 2-amino-1,3-propanediol.

Preservatives

Suitable preservatives are, for example, phenoxy ethanol, formaldehyde solution, parabens, pentanediol or sorbic acid, and the silver complexes known under the name Surfacins®, and also the other classes of substance listed in Annex 6, Part A and B of the Cosmetics Directive.

Perfume Oils-and Aromas

Perfume oils which may be mentioned are mixtures of natural and synthetic fragrances. Natural fragrances are extracts from flowers (lily, lavender, rose, jasmine, neroli, ylang-ylang), stems and leaves (geranium, patchouli, petitgrain), fruits (aniseed, coriander, cumin, juniper), fruit peels (bergamot lemon, orange), roots (mace, angelica, celery, cardamon, cestus, iris, calmus), woods (pinewood, sandalwood, guaiac wood, cedarwood, rosewood), herbs and grasses (tarragon, lemongrass, sage, thyme), needles and branches (spruce, fir, pine, dwarf-pine), resins and balsams (galbanum, elemi, benzoin, myrrh, olibanum, opoponax). Also suitable are animal raw materials, such as, for example, civet and castoreum. Typical synthetic fragrance compounds are products of the ester, ether, aldehyde, ketone, alcohol and hydrocarbon type. Fragrance compounds of the ester type are, for example, benzyl acetate, phenoxyethyl isobutyrate, p-tertbutylcyclohexyl acetate, linalyl acetate, dimethylbenzylcarbinyl acetate, phenylethyl acetate, linalyl benzoate, benzyl formate, ethylmethylphenyl glycinate, allyl cyclohexylpropionate, styrallyl propionate and benzyl salicylate. The ethers include, for example, benzyl ethyl ether, the aldehydes include, for example, the linear alkanals having 8 to 18 carbon atoms, citral, citronellal, citronellyloxyacetaldehyde, cyclamen aldehyde, hydroxycitronellal, lilial and bourgeonal, and the ketones include, for example, the ionones, α-isomethylionone and methyl cedryl ketone, the alcohols include anethole, citronellol, eugenol, isoeugenol, geraniol, linalool, phenylethyl alcohol and terpineol, and the hydrocarbons include mainly the terpanes and balsams. Preference is, however, given to using mixtures of different fragrances which together produce a pleasing fragrance note. Essential oils of relatively low volatility, which are mostly used as aroma components, are also suitable as perfume oils, e.g. sage oil, camomile oil, oil of cloves, melissa oil, mint oil, cinnamon leaf oil, linden blossom oil, juniper berry oil, vetiver oil, olibanum oil, galbanum oil, labolanum oil and lavandin oil. Preference is given to using bergamot oil, dihydromyrcenol, lilial, lyral, citronellol, phenylethyl alcohol, α-hexylcinnamaldehyde, geraniol, benzylacetone, cyclamen aldehyde, linalool, boisambrene forte, ambroxan, indole, hedione, sandelice, lemon oil, mandarin oil, orange oil, allyl amyl glycolate, cyclovertal, lavandin oil, clary sage oil, β-damascone, geranium oil bourbon, cyclohexyl salicylate, Vertofix coeur, iso-E-super, Fixolide NP, evernyl, iraldein gamma, phenylacetic acid, geranyl acetate, benzyl acetate, rose oxide, romilat, irotyl and floramat alone or in mixtures.

Suitable aromas are, for example, peppermint oil, spearmint oil, anise oil, star anise oil, caraway oil, eucalyptus oil, fennel oil, lemon oil, wintergreen oil, oil of cloves, menthol and the like.

Dyes

Dyes which can be used are the substances which are approved and suitable for cosmetic purposes, as are summarized, for example, in the publication "Kosmetische Farbemittel" [Cosmetic Colorants] from the Farbstoffkommission der Deutschen Forschungsgemeinschaft [Dyes Commission of the German Research Council], Verlag Chemie, Weinheim, 1984, pp. 81-106. Examples are cochineal red A (C.I.16255), patent blue V (C.I.42051), indigotin (C.I.73015), chlorophyllin (C.I.75810), quinoline yellow (C.I.47005), titanium dioxide (C.I.77891), indanthrene blue RS (C.I.69800) and madder lake (C.I.58000). As a luminescent dye, it is also possible for luminal to be present. These dyes are customarily used in concentrations of from 0.001 to 0.1% by weight, based on the total mixture.

The total amount of auxiliaries and additives can be 1 to 50% by weight, preferably 5 to 40% by weight, based on the compositions. The compositions can be prepared by customary cold or hot processes; preference is given to using the phase-inversion temperature method.

The following examples are illustrative of the invention and should not be construed in any manner whatsoever as limiting the scope of the present invention.

EXAMPLES

Example 1

Cosmetic Emulsion

| Trade name | INCI | % by weight |
|---|---|---|
| Emulgade® SE-PF (2) | Glyceryl Stearate (and) Ceteareth-20 (and) Ceteareth-12 (and) Cetearyl Alcohol (and) Cetyl palmitate | 6.00 |
| Lanette® O (2) | Cetearyl Alcohol | 2.50 |
| Cegesoft® C24 (2) | Ethyl hexyl palmitate | 6.00 |
| CeUol® PGL (2) | Hexyldecanol (and) Hexyldecyllaurate | 5.00 |
| Myritol® 312 (2) | Caprylic/Capric Trigylceride | 3.00 |
| DC 200-50cts (3) | Dimethicone | 1.00 |
| Deionized water | | add 100 |
| Keltrol T (4) | Xantham Gum | 0.20 |
| Elestab 50J (1) | Chlorphenesin (and) Methylparaben | 0.40 |
| Glycerine | | 4.00 |
| Carbopol980 (5) | 2% Carbomer | 15.00 |
| NaOH 10% | | 0.60 |
| Perfume ChampalineG10415611 (6) | | 0.10 |
| Oligopeptide | N-Acetyl-Tyr-Pro-Trp-Phe-NH$_2$ (SEQ ID NO: 3) | 0.0003 |

Example 2

Cosmetic Fluid Serum

| Trade name | INCI | % by weight |
|---|---|---|
| Elestab 50J[1] | Chlorphenesin (and) Methylparaben | 0.35 |
| Oligopeptide | H-Tyr-Pro-Phe-Phe-NH$_2$ (SEQ ID NO: 6) | 0.001 |
| Keltrol CGT[4] | Xanthan gum | 0.10 |
| Cosmedia SP[2] | Sodium Polyacrylate | 0.25 |
| Deionized Water | | add 100 |

Suppliers

[1] Laboratoires Serobiologiques;
[2] Cognis;
[3] Dow Corning;
[4] Kelco;
[5] Noveon,
[6] Robertet

Example 3

Cosmetic Emulsion with AHA

| Trade name | INCI | % by weight |
|---|---|---|
| I. Glycerin | | 2 |
| Butylene Glycol | | 1 |
| Veegum Ultra[1] | Magnesium Aluminium Silicate | 0.5 |
| Rhodicare XC[2] | Xantham Gum | 0.5 |
| Elestab CPN[3] | Chlorphenesin | 0.25 |
| Versene powder[4] | Tetradosium EDTA | 0.1 |
| Deionized Water | | add 100 |
| II. Eumulgin S2 | Steareth-2 | 2 |
| Eumulgin 821 | Steareth-21 | 2 |
| Lanette 18 | Stearyl Alcohol | 1.5 |
| Cutina MD | Glyceryl Stearate | 3 |
| Eusolex 2292[5] | Ethylhexyl Methoxycinnamate | 6 |
| Eusolex 9020[5] | Butyl Methoxydibenzoylmethane | 2 |
| Cetiol S | Diethylhexylcyclohexane | 5 |
| Eutanol G16 | Hexyldecanol | 3 |
| Eutanol G 3 | Octyldodecanol | |
| CreasiiiH CG[6] | Isohexadecane | 2 |
| DC 200, 100 cs[7] | Dimethicone | 0.75 |
| General R[3] | *Brassica Campestris* (Rapeseed) Sterols | 0.5 |
| III. Deionized Water | | 15 |

-continued

| Trade name | INCI | % by weight |
|---|---|---|
| Photonyl LS[3] | Arginine (and) Disodium Adenosine Triphosphate (and) Mannitol (and) Pyridoxine HCl RNA (and) Histidine HCl (and) Phenylalanine (and) Tyrosine | 1.5 |
| IV. Dry Flo Plus[8] | Aluminium Starch Octenylsuccinate | 3 |
| V. AHCare G60[3] | Glycolic acid (and) Aqua (and) Arginine | 10 |
| Ammoniac (sol. 20.5%) | | qs pH 3.5 |
| VI. Dennosaccharides HC[3] | Glycerin (and) Aqua (and) Glycosaminoglycans (and) GlycoQen | 2 |
| Powdy Dream 50-3770[9] | | 0.15 |
| VII. Oligopeptide | N-Acetyl-Tyr-Pro-Phe-Phe-NH$_2$ (SEQ ID NO: 4) | 0.001 |

Suppliers
[1]Vanderbilt,
[2]Rhodia,
[3]Laboratoires Serobiologiques;
[4]Brenntag,
[5]Merck,
[6]Cosmo Chem,
[7]Dow Corning,
[8]National Starch,
[9]Cognis Fragrances Example 4

Quali-quantitative composition of the Active Ingredient: Ac-YPFF-NH$_2$ (acetyl-Tyr-Pro-Phe-Phe-NH$_2$) (SEQ ID NO:4): 400 ppm in a solution water/glycerol 50/50 (w/w) was carried out.

Example 5

Protocol: Sensorial evaluation in vivo on 16 human volunteers of the soothing effect of an emulsion with 2% Active Ingredient according to example 4 versus placebo emulsion. The volunteers were trained to detect the levels of cutaneous sensibility at the heat. During this training, the cutaneous thermal sensitivity is evaluated by measures with "Thermal Sensory Analyser" (TSA). At the end of the training, 2 zones were delimited on the scapular back: one was treated by placebo emulsion and the other by emulsion with 2% Active Ingredient (a standardized application of 2 µl/cm$^2$). 120 minutes after application of the products, the perception of heat was evaluated by the volunteers according to 2 levels: "sensorial discomfort" and "painful". The results are the synthesis of the variations of temperatures observed for each level of sensitivity on the treated zone and the placebo zone.
Composition of the Tested Products:

| Emulsion with 2% Active Ingredient | |
|---|---|
| PHASE A | |
| Water | Add 100.00 |
| Propylene Glycol (and) Phenoxyethanol (and) Chlorphenesin (and) Methylparaben | 2.50 |
| CetearylIsononanoate (and) Ceteareth-20 (and) Cetearyl Alcohol (and) Glyceryl Stearate (and) Glycerin (and) Ceteareth-12 (and) Cetyl Palmitate | 10.00 |
| Xanthan Gum | 0.20 |
| Sodium Polyacrylate (and) Hydrogenated Polydecene (and) PPG-5 Laureth-5 | 1.20 |
| Mica (and) Titanium Dioxide | 1.00 |
| PHASE B | |
| Dicaprylyl Carbonate | 3.00 |
| PHASE C | |
| Active Ingredient | 2.00 |

| Emulsion without active ingredient (placebo) | |
|---|---|
| PHASE A | |
| Water | Add 100.00 |
| Propylene Glycol (and) Phenoxyethanol (and) Chlorphenesin (and) Methylparaben | 2.50 |
| CetearylIsononanoate (and) Ceteareth-20 (and) Cetearyl Alcohol (and) Glyceryl Stearate (and) Glycerin (and) Ceteareth-12 (and) Cetyl Palmitate | 10.00 |
| Xanthan Gum | 0.20 |
| Sodium Polyacrylate (and) Hydrogenated Polydecene (and) PPG-5 Laureth-5 | 1.20 |
| 30 Mica (and) Titanium Dioxide | 1.00 |
| PHASE B | |
| Dicaprylyl Carbonate | 3.00 |

| Results | | |
|---|---|---|
| | Sensorial discomfort (° C.) | Painful (° C.) |
| Variations in perception of temperature on the zone treated with emulsion containing 2% Active Ingredient based on example 4 (before and 120 minutes after application of the products) (AI) | 2.5 ± 0.6 | 1.7 ± 0.4 |
| Variations in perception of temperature on the zone treated with placebo emulsion (before and 120 minutes after application of the products) (PL) | 1.3 ± 0.6 | 1.2 ± 0.5 |
| Difference: AI − PL | 1.3 ± 0.5 | 0.5 ± 0.3 |

120 minutes after the application of the emulsion with 2% Active Ingredient and in comparison to the placebo zone, the perception of heat significantly decreased for level "discomfort" and painful". These results demonstrated a soothing effect 120 minutes after the application of the emulsion with 2% active ingredient according to example 4.

What is claimed is:

1. A method for reducing skin discomfort and/or pain due to an irritating cosmetic agent in a cosmetic composition comprising administering to skin in need thereof a cosmetic composition which comprises
   a) an oligopeptide according to formula (I) and/or (II):

$$R_1\text{-Tyr-Pro-Trp-Phe-NH}_2 \quad \text{(I)} \quad \text{(SEQ ID NO: 1)}$$
   $$R_1\text{-Tyr-Pro-Phe-Phe-NH}_2 \quad \text{(II)} \quad \text{(SEQ ID NO: 2)}$$

wherein $R_1$ is linked to the $NH_2$-group of the amino-terminal portion of Tyr and is selected from the group consisting of:
   (i) —H;
   (ii) a linear saturated or unsaturated or branched saturated or unsaturated acyl group having 1 to 24 carbon atoms, which acyl group can be functionalized by a —OH, —SH, —COOH or —CONH$_2$ group; and
   (iii) a sterol or a sphingolipid group which is linked to the amino terminal portion of Tyr by a bifunctional linker;
   b) an irritating cosmetic agent; and
   c) optionally, an additive or auxiliary suitable for use in a cosmetic composition;
   wherein the oligopeptide is present in the composition in an amount sufficient to reduce discomfort and/or pain due to the irritating cosmetic agent when the cosmetic composition is administered cutaneously.

2. The method of claim 1, wherein the oligopeptide has a sequence N-Acetyl-Tyr-Pro-Trp-Phe-NH$_2$ (SEQ ID NO:3) or N-Acetyl-Tyr-Pro-Phe-Phe-NH$_2$ (SEQ ID NO:4.

3. The method of claim 1, wherein the oligopeptide is present in an amount of from about 0.001 to 1,000 ppm based by weight of the composition.

4. The method of claim 3, wherein the oligopeptide is present in an amount of about 0.05 to 500 ppm.

5. The method of claim 4, wherein the oligopeptide is present in an amount of about 0.5 to 100 ppm.

6. The method of claim 1, wherein the composition is administered to reduce thermal sensitivity of the skin.

7. The method of claim 1, wherein the composition is administered to prevent symptoms of skin discomfort and/or pain due to an irritating cosmetic agent.

8. The method of claim 1, wherein the composition is administered to ameliorate existing symptoms of skin discomfort and/or pain due to an irritating cosmetic agent.

9. The method of claim 1, wherein the composition is administered to sensitive skin.

10. The method of claim 1 wherein the irritating cosmetic agent is an alpha-hydroxy or beta-hydroxy acid or a salt or ester thereof.

11. The method of claim 10, wherein the alpha-hydroxy acid is selected from C2 to C12 alpha-hydroxy acids and esters thereof with a C2 to C24 alcohol.

12. The method of claim 10, wherein the beta-hydroxy acid is selected from C2 to C12 beta-hydroxy acids and esters thereof with a C2 to C24 alcohol.

13. The method of claim 10, wherein the acid is selected from the group consisting of lactic acid, citric acid, glycolic acid, gentisic acid, salicylic acid, gluconic acid and heptonic acid.

14. The method of claim 1 wherein the irritating cosmetic agent is a retinoid.

15. The method of claim 14, wherein the retinoid is selected from the group consisting of retinol, retinal, retinoic acid, retinyl acetate, retinyl palmitate and retinyl ascorbate.

16. A cosmetic composition which comprises:
   a) an oligopeptide according to formula (I) and/or (II) of:

```
                                          (SEQ ID NO: 1)
       R₁-Tyr-Pro-Trp-Phe-NH₂  (I)

(SEQ ID NO: 2)
       R₁-Tyr-Pro-Phe-Phe-NH₂  (II)
   ``` wherein $R_1$ is linked to the $NH_2$-group of the amino-terminal portion of Tyr and is selected from the group consisting of:
   (i) —H;
   (ii) a linear saturated or unsaturated or branched saturated or unsaturated acyl group having 1 to 24 carbon atoms, which acyl group can be functionalized by a —OH, —SH, —COOH or —CONH₂ group; and
   (iii) a sterol or a sphingolipid group which is linked to the amino terminal portion of Tyr by a bifunctional linker;
   b) an irritating cosmetic agent; and
   c) optionally, an additive or auxiliary suitable for use in a cosmetic composition;
   wherein the oligopeptide is present in the composition in an amount sufficient to reduce discomfort and/or pain due to the irritating cosmetic agent when the cosmetic composition is administered cutaneously.

17. The cosmetic composition of claim 16, wherein the oligopeptide has a sequence N-Acetyl-Tyr-Pro-Trp-Phe-NH₂ (SEQ ID NO:3) or N-Acetyl-Tyr-Pro-Phe-Phe-NH₂ (SEQ ID NO:4).

18. The cosmetic composition of claim 16, wherein the irritating cosmetic agent is an alpha-hydroxy or beta-hydroxy acid or a salt or ester thereof.

19. The cosmetic composition of claim 16, wherein the irritating cosmetic agent is a retinoid.

20. The cosmetic composition of claim 16, wherein the oligopeptides is present in an amount of from about 0.5 to 100 ppm.

\* \* \* \* \*

SEQUENCE LISTING

<160> NUMBER OF SEQ ID NOS: 6

<210> SEQ ID NO 1
<211> LENGTH: 4
<212> TYPE: PRT
<213> ORGANISM: Artificial Sequence
<220> FEATURE:
<223> OTHER INFORMATION: oligopeptide
<220> FEATURE:
<221> NAME/KEY: MISC_FEATURE
<222> LOCATION: (1)..(1)
<223> OTHER INFORMATION: R1 linked at N-terminal
<220> FEATURE:
<221> NAME/KEY: MOD_RES
<222> LOCATION: (4)..(4)
<223> OTHER INFORMATION: AMIDATION

<400> SEQUENCE: 1

Tyr Pro Trp Phe
1

<210> SEQ ID NO 2
<211> LENGTH: 4
<212> TYPE: PRT
<213> ORGANISM: Artificial Sequence
<220> FEATURE:
<223> OTHER INFORMATION: oligopeptide
<220> FEATURE:
<221> NAME/KEY: MISC_FEATURE
<222> LOCATION: (1)..(1)
<223> OTHER INFORMATION: R1 linked at N-terminal
<220> FEATURE:
<221> NAME/KEY: MOD_RES
<222> LOCATION: (4)..(4)
<223> OTHER INFORMATION: AMIDATION

<400> SEQUENCE: 2

Tyr Pro Phe Phe
1

<210> SEQ ID NO 3
<211> LENGTH: 4
<212> TYPE: PRT
<213> ORGANISM: Artificial Sequence
<220> FEATURE:
<223> OTHER INFORMATION: oligopeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (4)..(4)
<223> OTHER INFORMATION: AMIDATION

<400> SEQUENCE: 3

Tyr Pro Trp Phe
1

<210> SEQ ID NO 4
<211> LENGTH: 4
<212> TYPE: PRT
<213> ORGANISM: Artificial Sequence
<220> FEATURE:
<223> OTHER INFORMATION: oligopeptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES

```
<222> LOCATION: (4)..(4)
<223> OTHER INFORMATION: AMIDATION

<400> SEQUENCE: 4

Tyr Pro Phe Phe
1

<210> SEQ ID NO 5
<211> LENGTH: 4
<212> TYPE: PRT
<213> ORGANISM: Artificial Sequence
<220> FEATURE:
<223> OTHER INFORMATION: oligopeptide
<220> FEATURE:
<221> NAME/KEY: MOD_RES
<222> LOCATION: (4)..(4)
<223> OTHER INFORMATION: AMIDATION

<400> SEQUENCE: 5

Tyr Pro Trp Phe
1

<210> SEQ ID NO 6
<211> LENGTH: 4
<212> TYPE: PRT
<213> ORGANISM: Artificial Sequence
<220> FEATURE:
<223> OTHER INFORMATION: oligopeptide
<220> FEATURE:
<221> NAME/KEY: MOD_RES
<222> LOCATION: (4)..(4)
<223> OTHER INFORMATION: AMIDATION

<400> SEQUENCE: 6

Tyr Pro Phe Phe
1
```